United States Patent
Kimoto et al.

(10) Patent No.: US 10,299,752 B2
(45) Date of Patent: May 28, 2019

(54) MEDICAL IMAGE PROCESSING APPARATUS, X-RAY CT APPARATUS, AND IMAGE PROCESSING METHOD

(71) Applicant: Toshiba Medical Systems Corporation, Otawara-shi (JP)

(72) Inventors: Tatsuya Kimoto, Utsunomiya (JP); Shigeharu Ohyu, Yaita (JP); Yasuko Fujisawa, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 15/139,770

(22) Filed: Apr. 27, 2016

(65) Prior Publication Data

US 2016/0310095 A1 Oct. 27, 2016

(30) Foreign Application Priority Data

Apr. 27, 2015 (JP) ................................ 2015-090640
Feb. 23, 2016 (JP) ................................ 2016-031674

(51) Int. Cl.
*G06K 9/00* (2006.01)
*A61B 6/00* (2006.01)
(Continued)

(52) U.S. Cl.
CPC .............. *A61B 6/5217* (2013.01); *A61B 6/50* (2013.01); *G06T 7/62* (2017.01); *A61B 6/032* (2013.01);
(Continued)

(58) Field of Classification Search
CPC ... A61B 5/0013; A61B 5/0033; A61B 5/0073; A61B 5/08; A61B 5/0813; A61B 5/082;
(Continued)

(56) References Cited

U.S. PATENT DOCUMENTS

| 8,396,268 B2 * | 3/2013 | Zabair ...................... G06K 9/00 128/922 |
| 8,483,456 B2 * | 7/2013 | Nagatsuka ............... A61B 5/08 382/128 |

(Continued)

FOREIGN PATENT DOCUMENTS

JP 2014-210171 11/2014

*Primary Examiner* — Jose L Couso
(74) *Attorney, Agent, or Firm* — Oblon, McClelland, Maier & Neustadt, L.L.P.

(57) ABSTRACT

A medical image processing apparatus according to an embodiment includes storage circuitry, image data processing circuitry, and association circuitry. The storage circuitry stores therein pieces of image data on a subject obtained at a plurality of time phases from a medical image diagnostic apparatus. The image data processing circuitry calculates an index value obtained by comparing a pixel value of image data of a reference time phase among the pieces of image data of the time phases and a pixel value of each of the pieces of image data of the time phases. The association circuitry selects at least one of the pieces of image data of the time phases based on the index value calculated for each of the time phases and associates the one piece of image data with a breathing time phase in at least one of inspiration and expiration of the subject.

19 Claims, 10 Drawing Sheets

(51) Int. Cl.
*G06T 7/62* (2017.01)
*A61B 6/03* (2006.01)
(52) U.S. Cl.
CPC ............... *G06T 2207/10081* (2013.01); *G06T 2207/20224* (2013.01); *G06T 2207/30061* (2013.01)
(58) Field of Classification Search
CPC ....... A61B 5/087; A61B 5/113; A61B 5/7285; A61B 5/7289; A61B 5/7292; A61B 6/03–6/032; A61B 6/037; A61B 6/469; A61B 6/486; A61B 6/50; A61B 6/5205; A61B 6/5217; A61B 6/5235; A61B 6/5264; A61B 6/5288; A61B 6/541; A61B 8/13; A61B 8/543; A61B 2090/3735; A61B 2090/376–2090/3764; A61B 2090/364; G06T 5/50; G06T 7/0012; G06T 7/0016; G06T 7/254; G06T 11/003; G06T 11/005; G06T 11/008; G06T 2207/10064; G06T 2207/10072–2207/10088; G06T 2207/10101–2207/10108; G06T 2207/10116–2207/10124; G06T 2207/30004; G06T 2207/30061; G06T 2207/20224; G06T 2210/41; G06T 2211/40; G06T 2211/408–2211/436; G06K 7/1099; G06K 9/6293; G01N 23/043; G01N 23/046; G01R 33/56308–33/56316; G01R 33/56509; G01R 33/5673; A61N 5/10; A61N 5/1048; A61N 2005/1059; A61N 2005/1062; Y10S 378/901; H04N 5/32; H04N 5/3205; H04N 5/325; H04N 19/137

See application file for complete search history.

(56) References Cited

U.S. PATENT DOCUMENTS

| | | | |
|---|---|---|---|
| 9,064,302 B2* | 6/2015 | Muraoka | A61B 6/507 |
| 9,117,287 B2* | 8/2015 | Masumoto | A61B 6/032 |
| 9,125,621 B2* | 9/2015 | Nagatsuka | A61B 5/08 |
| 9,198,628 B2* | 12/2015 | Shimada | A61B 6/4291 |
| 9,582,906 B2* | 2/2017 | Ra | G06T 11/005 |
| 9,757,075 B2* | 9/2017 | Mukumoto | A61B 6/03 |
| 2013/0331725 A1* | 12/2013 | Noji | A61B 6/5217 600/534 |
| 2014/0275704 A1* | 9/2014 | Zhang | A61N 5/1037 600/1 |
| 2016/0022240 A1 | 1/2016 | Yamagata et al. | |
| 2016/0121140 A1* | 5/2016 | Li | A61N 5/1049 600/407 |

* cited by examiner

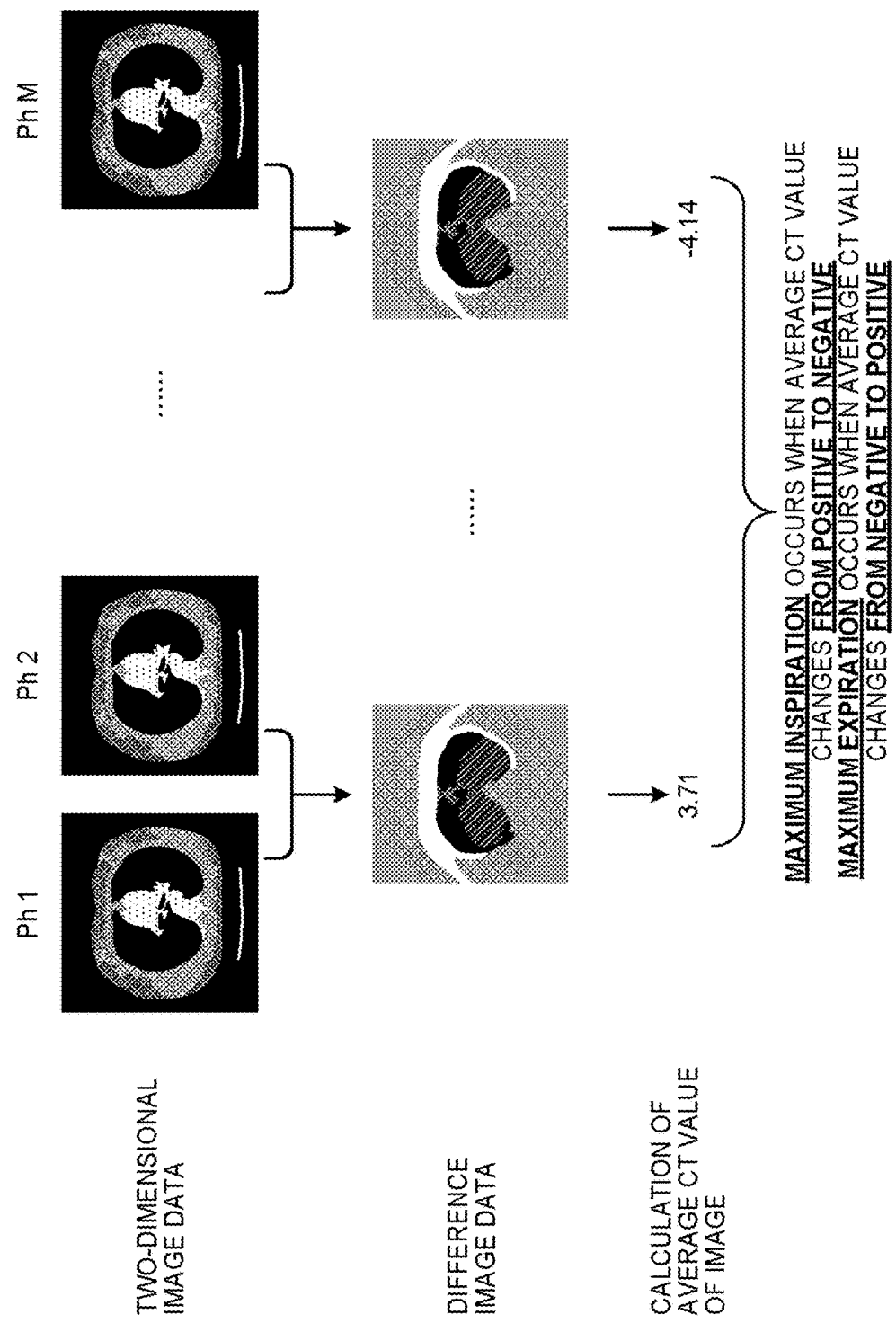

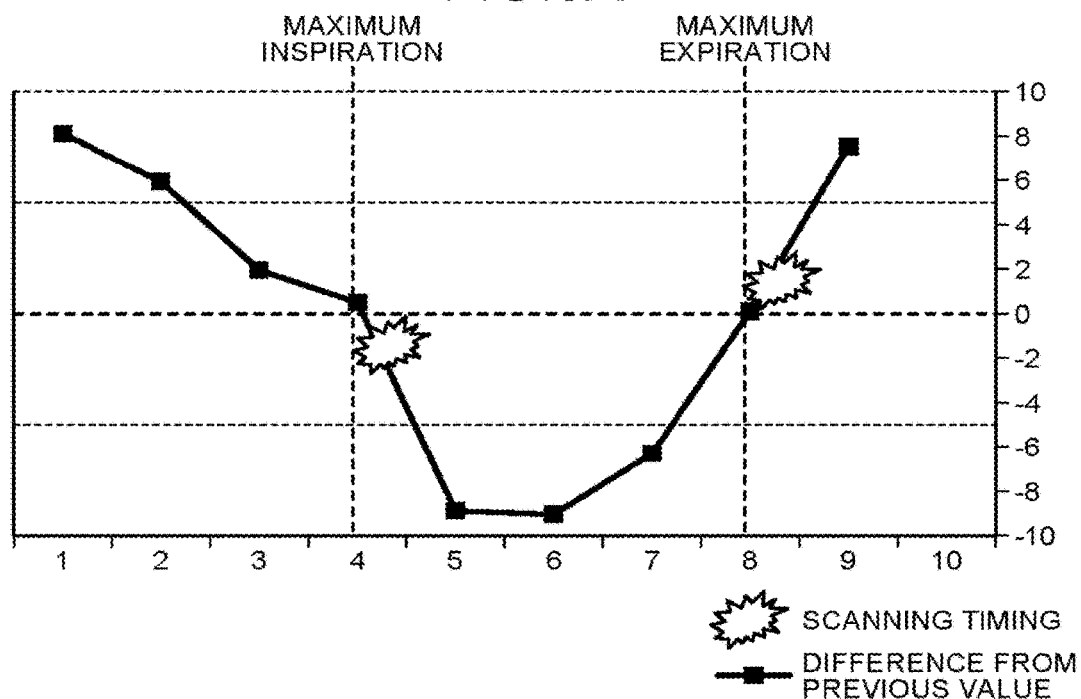
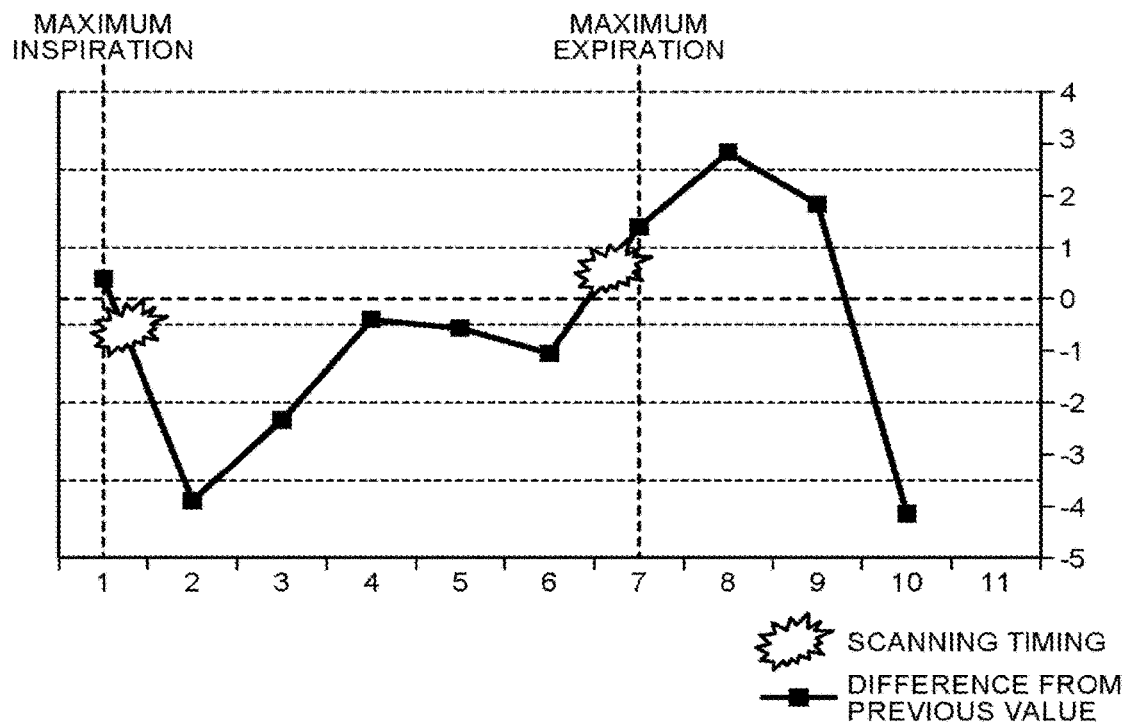

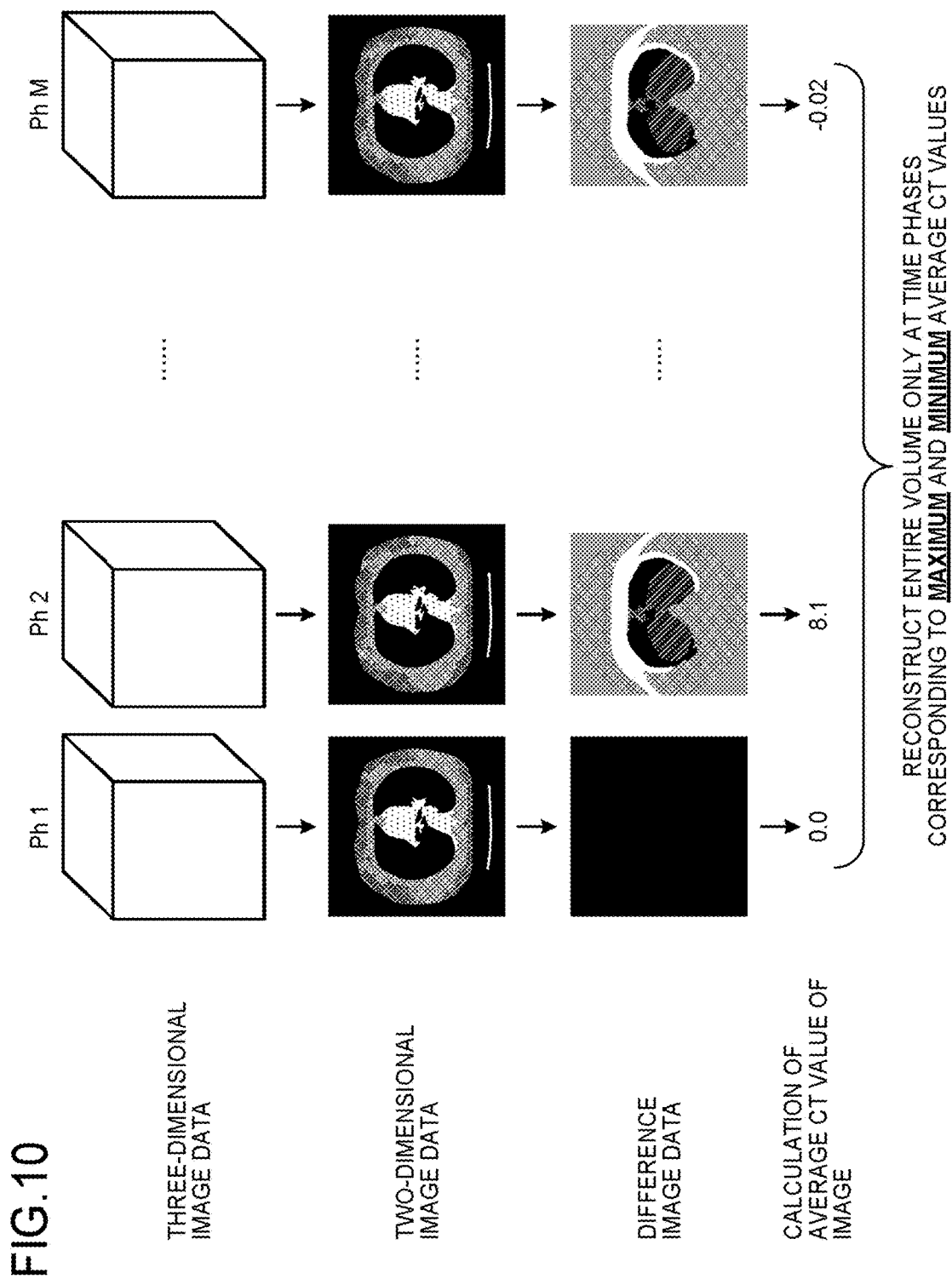

AVERAGE CT VALUE IN LUNG FIELD

DIFFERENCE FROM REFERENCE

MEDICAL IMAGE PROCESSING APPARATUS, X-RAY CT APPARATUS, AND IMAGE PROCESSING METHOD

CROSS-REFERENCE TO RELATED APPLICATIONS

This application is based upon and claims the benefit of priority from Japanese Patent Application No. 2015-090640, filed on Apr. 27, 2015; and Japanese Patent Application No. 2016-031674, filed on Feb. 23, 2016, the entire contents of all of which are incorporated herein by reference.

FIELD

Embodiments described herein relate generally to a medical image processing apparatus, an X-ray computed tomography (CT) apparatus, and an image processing method.

BACKGROUND

Diagnosis on the bronchi of a subject is performed using a three-dimensional image data obtained by imaging the chest of the subject using a medical image diagnostic apparatus such as an X-ray CT apparatus. The diagnosis on the bronchi requires observation of temporal change of the bronchi in association with a breathing cycle. The cycle of breathing can be obtained by extracting a lung field region from three-dimensional image data and calculating the volume thereof.

However, the calculation of the volume of the lung field associated with the temporal change of the bronchi requires extraction of the lung field region from three-dimensional image data of a plurality of time phases in one cycle of breathing, which results in an increased time for processing image data.

BRIEF DESCRIPTION OF THE DRAWINGS

FIG. 8 is a diagram illustrating the second embodiment.
FIG. 9A is a diagram illustrating timing of breathing synchronous scanning according to the second embodiment;
FIG. 9B is another diagram illustrating the timing of the breathing synchronous scanning according to the second embodiment;
FIG. 10 is a diagram illustrating a third embodiment.

DETAILED DESCRIPTION

Embodiments will be described below with reference to the accompanying drawings.

A medical image processing apparatus according to an embodiment includes storage circuitry, image data processing circuitry, and association circuitry. The storage circuitry stores therein pieces of image data on a subject obtained at a plurality of time phases from a medical image diagnostic apparatus. The image data processing circuitry calculates an index value obtained by comparing a pixel value of image data of a reference time phase among the pieces of image data of the time phases and a pixel value of each of the pieces of image data of the time phases. The association circuitry selects at least one of the pieces of image data of the time phases based on the index value calculated for each of the time phases and associates the one piece of image data with a breathing time phase in at least one of inspiration and expiration of the subject.

First Embodiment

Figure 1:
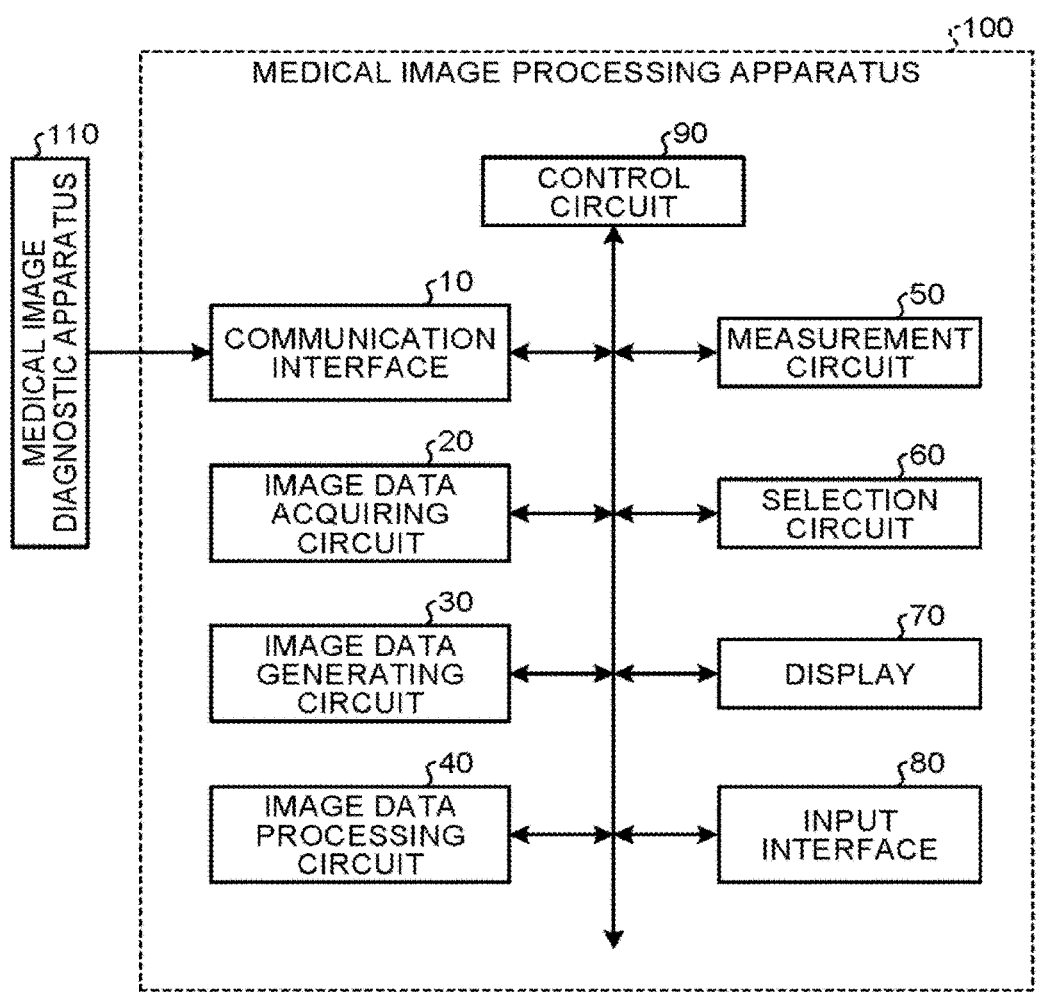
FIG. 1 is a block diagram of the configuration of a medical image processing apparatus according to a first embodiment.

FIG. 1 is a block diagram of the configuration of a medical image processing apparatus according to a first embodiment. This medical image processing apparatus 100 includes a communication interface 10 that receives three-dimensional image data of a plurality of time phases in at least one cycle of breathing obtained by imaging the chest of a subject and transmitted from a medical image diagnostic apparatus 110 such as an X-ray CT apparatus. The medical image processing apparatus 100 further includes an image data acquiring circuit 20 that acquires the three-dimensional image data of each time phase received by the communication interface 10.

The medical image processing apparatus 100 further includes an image data generating circuit 30 that generates two-dimensional image data illustrating a cross-section at a specified position in a body axis direction of the subject from the three-dimensional image data of each time phase acquired by the image data acquiring circuit 20. The medical image processing apparatus 100 further includes an image data processing circuit 40 that processes the two-dimensional image data of each time phase generated by the image data generating circuit 30. The medical image processing apparatus 100 further includes a measurement circuit 50 that measures, for example, the pixel value and area of the image data processed by the image data processing circuit 40. The image data processing circuit 40 and the measurement circuit 50 are also collectively referred to as image data processing circuitry.

The medical image processing apparatus 100 may be provided with internal or external storage circuitry, and the three-dimensional image data acquired by the image data acquiring circuit 20 may be stored in this internal or external storage circuitry and read by the image data generating circuit 30 to generate two-dimensional image data. In other words, the storage circuitry stores therein image data on a subject P obtained at a plurality of time phases from the medical image diagnostic apparatus 110.

The medical image processing apparatus 100 further includes a selection circuit 60 that selects a predetermined time phase in inspiration and expiration from among a plurality of time phases in the breathing cycle based on a value measured by the measurement circuit 50. The selection circuit 60 is also referred to as association circuitry. The medical image processing apparatus 100 further includes a display 70 that displays, for example, the three-dimensional image data acquired by the image data acquiring circuit 20, the two-dimensional image data generated by the image data generating circuit 30, and the image data processed by the image data processing circuit 40.

The medical image processing apparatus 100 includes an input interface 80 that performs, for example, inputting to execute the generation of the two-dimensional image data by the image data generating circuit 30, the processing of the two-dimensional image data by the image data processing circuit 40, and the measurement by the measurement circuit 50. The medical image processing apparatus 100 further includes a control circuit 90 that integrally controls the communication interface 10, the image data acquiring circuit 20, the image data generating circuit 30, the image data processing circuit 40, the measurement circuit 50, the selection circuit 60, the display 70, and the input interface 80.

The following describes an exemplary operation of the medical image processing apparatus 100 with reference to FIGS. 1 to 4.

Figure 2:
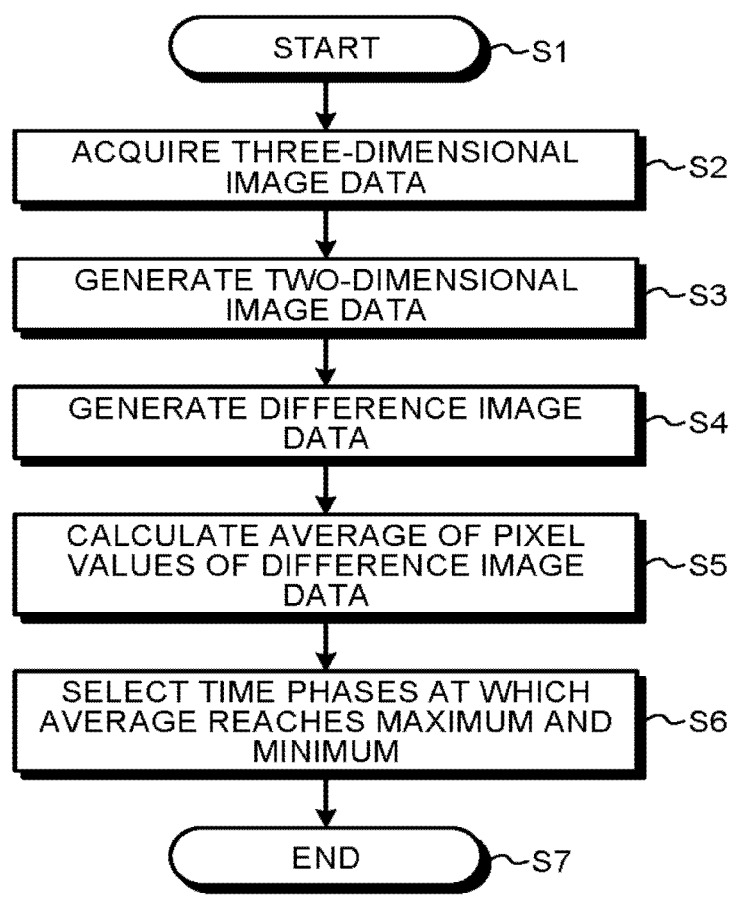
FIG. 2 is a flowchart of an operation of the medical image processing apparatus according to the first embodiment.

FIG. 2 is a flowchart of the operation of the medical image processing apparatus 100.

When the communication interface 10 receives the three-dimensional image data of a plurality of time phases in the breathing cycle obtained by imaging the chest including the lungs and bronchi of the subject and transmitted from the medical image diagnostic apparatus 110, the medical image processing apparatus 100 starts its operation (step S1).

Figure 3:
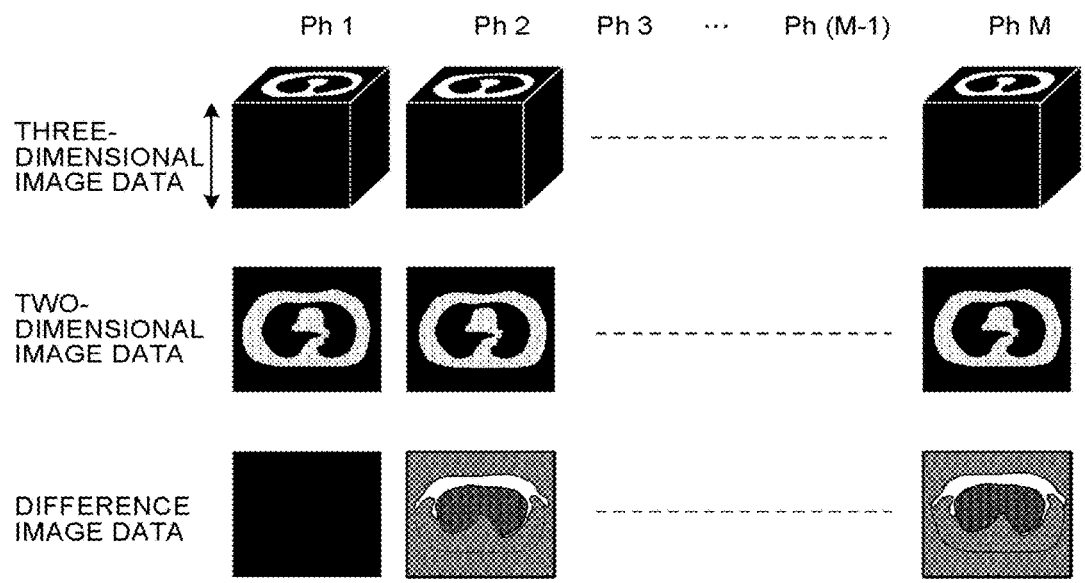
FIG. 3 illustrates an example of three-dimensional image data and two-dimensional image data of each time phase in a breathing cycle according to the first embodiment, and difference image data of each time phase generated by difference processing on the two-dimensional image data of the time phase and the two-dimensional image data of a first time phase.

Through the above-described reception by the communication interface 10, the image data acquiring circuit 20 acquires three-dimensional image data (volume data, for example) of first time phase Ph1 to M-th time phase PhM as M divisions (M is a positive integer) of one breathing cycle, which are the time phases in the breathing cycle obtained from the medical image diagnostic apparatus 110, as illustrated in FIG. 3 (step S2).

The image data processing circuit 40 reads out the three-dimensional image data of any one of the time phases in accordance with an input for specifying a time phase from the input interface 80 for observation of the bronchi of the subject, and extracts any pixel having a pixel value in a predetermined range from a bronchial region. Subsequently, the image data processing circuit 40 generates three-dimensional image data illustrating the bronchi of the subject by, for example, a volume rendering method and displays this three-dimensional image data on the display 70.

Upon an input for specifying a desired position in a bronchial pathway direction for the three-dimensional image data displayed on the display 70 through the input interface 80, as illustrated in FIG. 3, the image data generating circuit 30 generates, from the three-dimensional image data of the first time phase Ph1 to the M-th time phase PhM acquired by the image data acquiring circuit 20, two-dimensional image data illustrating a cross-section at, for example, the central position corresponding to this specifying input in the body axis direction illustrated with an arrow (step S3).

When a plurality of pieces of two-dimensional image data of each of the first time phase Ph1 to the M-th time phase PhM in the breathing cycle are available from the medical image diagnostic apparatus 110, the image data generating circuit 30 reconstructs the pieces of two-dimensional image data of the first time phase Ph1 to the M-th time phase PhM to generate three-dimensional image data of the first time phase Ph1 to the M-th time phase PhM. The image data generating circuit 30 also selects two-dimensional image data at the position corresponding to a specifying input in the body axis direction from among the pieces of two-dimensional image data of each of the first time phase Ph1 to the M-th time phase PhM.

The image data processing circuit 40 processes the pieces of two-dimensional image data of the first time phase Ph1 to the M-th time phase PhM based on, for example, the two-dimensional image data of the first time phase Ph1 that has been set as a reference time phase in advance from among the pieces of two-dimensional image data of the first time phase Ph1 to the M-th time phase PhM generated by the image data generating circuit 30. Then, the image data processing circuit 40 generates difference image data of the first time phase Ph1 to the M-th time phase PhM by difference processing on each of the pieces of two-dimensional image data of the first time phase Ph1 to the M-th time phase PhM and the two-dimensional image data of the first time phase Ph1, as illustrated in FIG. 3 (step S4).

When the pieces of two-dimensional image data of the first time phase Ph1 to the M-th time phase PhM include data of a region other than a lung field region and a bronchial region, the image data processing circuit 40 performs the difference processing for the entire region including the other region.

In the difference processing, the difference of the two-dimensional image data of the first time phase Ph1 from the two-dimensional image data of the first time phase Ph1 is calculated to generate the difference image data of the first time phase Ph1. The difference of the two-dimensional image data of the second time phase Ph2 from the two-dimensional image data of the first time phase Ph1 is calculated to generate the difference image data of the second time phase Ph2, and the difference of the two-dimensional image data of the third time phase Ph3 from the two-dimensional image data of the first time phase Ph1 is calculated to generate the difference image data of the third time phase Ph3. The difference of the two-dimensional image data of the (M−1)-th time phase Ph(M−1) from the two-dimensional image data of the first time phase Ph1 is calculated to generate the difference image data of the (M−1)-th time phase Ph(M−1), and the difference of the two-dimensional image data of the M-th time phase PhM from the two-dimensional image data of the first time phase Ph1 is calculated to generate the difference image data of the M-th time phase PhM.

The measurement circuit 50 calculates an index value obtained by comparing the pixel value of image data of a reference time phase among pieces of image data of a plurality of time phases and the pixel value of each piece of image data of the time phases. For example, the measurement circuit 50 calculates the average of the pixel values of the entire difference image data of the first time phase Ph1 to the M-th time phase PhM generated by the processing in the image data processing circuit 40 (step S5).

Figure 4:
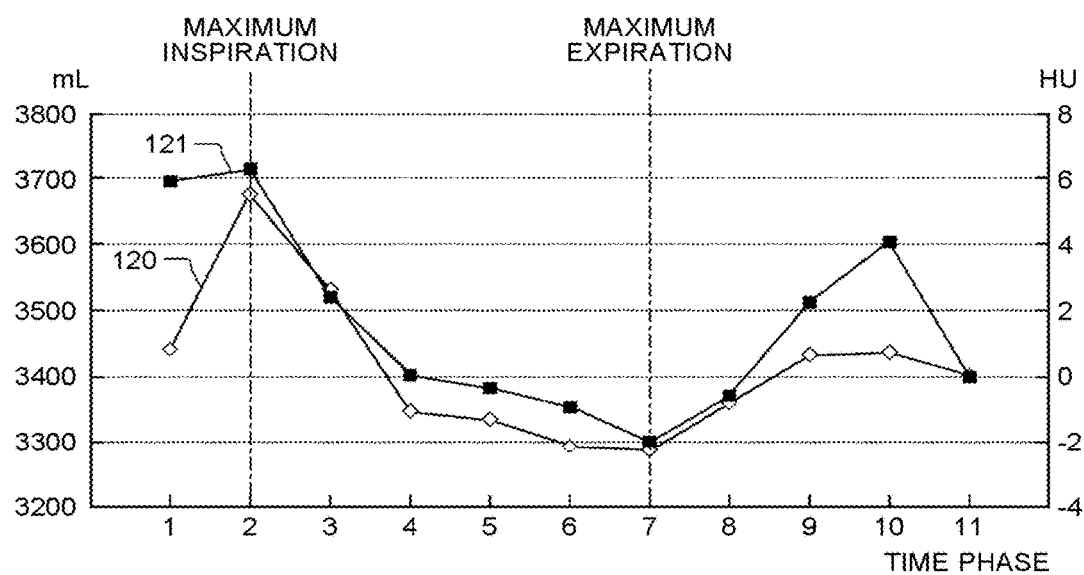
FIG. 4 is a graph illustrating a relation between the volume of a lung field and the average of pixel values of the difference image data of each time phase generated by difference processing on the two-dimensional image data of the time phase and the two-dimensional image data of the first time phase according to the first embodiment.

FIG. 4 is a graph illustrating a relation between the volume of the lung field and the average of the pixel values of the difference image data of each time phase. These graphs 120 and 121 were produced based on two-dimensional image data illustrating a cross-section at a predetermined position of three-dimensional image data of first to eleventh time phases as 11 divisions of one breathing cycle obtained by imaging the chest of the subject using the medical image diagnostic apparatus 110.

The graph 120 represents the volume of the lung field at the first to the eleventh time phases. The volume of the lung field is the maximum at the second time phase and the minimum at the seventh time phase. The graph 121 represents the average of the CT values of the difference image data of the first to the eleventh time phases when the pixel value of the two-dimensional image data of the first to the eleventh time phases is converted into a CT value in "HU" (Hounsfield unit) and the eleventh time phase is used as a reference time phase. The average of the CT values is the maximum at the second time phase and the minimum at the seventh time phase.

As described above, the inventors have found that the average of the CT values, which are the pixel values, of the difference image data is the maximum at the time phase of maximum inspiration at which the volume of the lung field is the maximum. The inventors have also found that the average of the pixel values of the difference image data is the minimum at the time phase of maximum expiration at which the volume of the lung field is the minimum.

The selection circuit 60 selects a predetermined time phase in at least one of inspiration and expiration from among the first time phase Ph1 to the M-th time phase PhM in the breathing cycle based on the pixel values of the entire difference image data of the first time phase Ph1 to the M-th time phase PhM illustrated in FIG. 3. In this selection, a time phase of difference image data having the maximum average of the pixel values is selected as the time phase of the maximum inspiration of the subject, and the time phase of difference image data having the minimum average of the pixel values is selected as the time phase of the maximum expiration of the subject (step S6).

As described above, it is possible to easily determine the time phases of the maximum inspiration and the maximum expiration without extracting the lung field region from three-dimensional image data, thereby achieving a shortened time for processing image data and achieving an improved throughput.

Then, the image data processing circuit 40 extracts any pixel in the bronchi region included in the two-dimensional image data of the time phases of the maximum inspiration and the maximum expiration selected by the selection circuit 60. The measurement circuit 50 calculates, for example, the cross-sectional area of the bronchial region extracted by the image data processing circuit 40, and displays the cross-sectional area on the display 70.

The display 70 displays thereon, for example, three-dimensional image data illustrating the bronchi of the subject, a marker indicating a specified position in the bronchial pathway direction, the pieces of two-dimensional image data of the first time phase Ph1 to the M-th time phase PhM, identification information for identifying the time phases of the maximum inspiration and the maximum expiration among the first time phase Ph1 to the M-th time phase PhM, and the cross-sectional areas of the bronchi at the maximum inspiration and the maximum expiration.

Modification of First Embodiment

Figure 5:
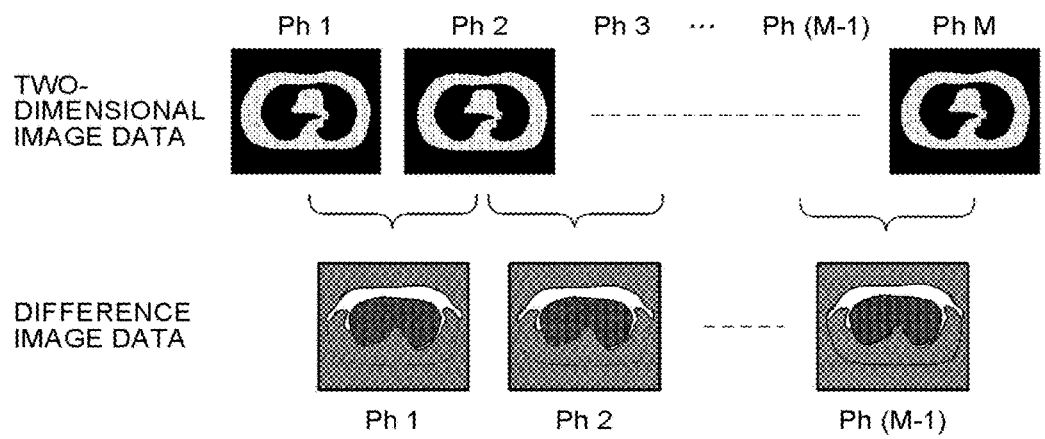
FIG. 5 illustrates exemplary difference image data of each time phase generated by difference processing on two-dimensional image data of two time phases adjacent to each other in the breathing cycle according to the first embodiment.

The first embodiment is not a limiting example, and may be achieved as follows. As illustrated in FIG. 5, one of two time phases adjacent to each other among the first time phase Ph1 to the M-th time phase PhM is set as a reference time phase, and difference processing is performed on the two-dimensional image data of the other time phase among the first time phase Ph1 to the (M−1)-th time phase Ph(M−1) and the two-dimensional image data of the reference time phase. In this calculation, the difference of the two-dimensional image data of the second time phase Ph2 from the two-dimensional image data of the first time phase Ph1 is calculated to generate the difference image data of the first time phase Ph1. In addition, the difference of the two-dimensional image data of the third time phase Ph3 from the two-dimensional image data of the second time phase Ph2 is calculated to generate the difference image data of the second time phase Ph2. In addition, the difference of the two-dimensional image data of the M-th time phase PhM from the two-dimensional image data of the (M−1)-th time phase Ph(M−1) is calculated to generate the difference image data of the (M−1)-th time phase. Accordingly, the difference image data of the first time phase Ph1 to the (M−1)-th time phase Ph(M−1) is generated.

Figure 6:
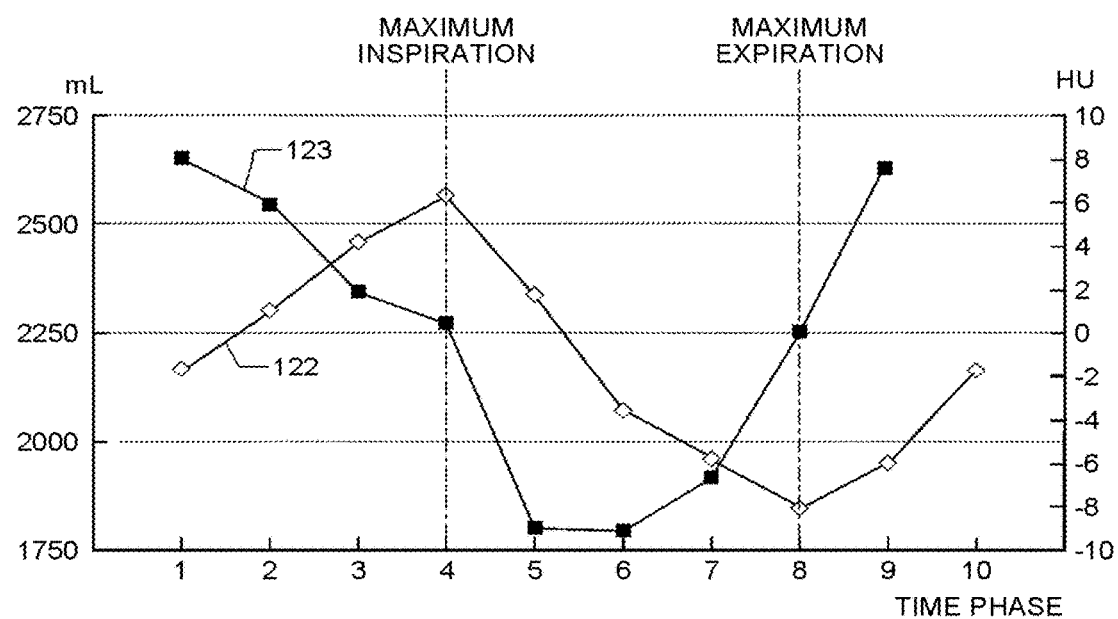
FIG. 6 is a graph illustrating a relation between the volume of the lung field of each time phase and the average of pixel values of difference image data of each time phase generated by difference processing on two-dimensional image data of two time phases adjacent to each other according to the first embodiment.

FIG. 6 is a graph illustrating a relation between the volume of the lung field of each time phase and the average of the pixel values of the difference image data of each time phase generated by the difference processing on the two-dimensional image data of two time phases adjacent to each other. These graphs 122 and 123 were produced based on two-dimensional image data illustrating a cross-section at a predetermined position in the three-dimensional image data of first to tenth time phases as 10 divisions of one breathing cycle obtained by imaging the chest of the subject using the medical image diagnostic apparatus 110.

The graph 122 illustrates the volume of the lung field at the first to the tenth time phases of the breathing cycle. The volume of the lung field is the maximum at the fourth time phase and the minimum at the eighth time phase. The graph 123 illustrates the average of the CT values of the difference image data of the first to the ninth time phases obtained by subtracting the two-dimensional image data of the later one of two time phases adjacent to each other among the first to the tenth time phases from the two-dimensional image data of the earlier time phase among the first to the tenth time phases when the later time phase is set as a reference time phase. The average of the CT values is the maximum at the fourth time phase and the minimum at the eighth time phase.

As described above, the inventors have found that the average of the pixel values of the difference image data decreases to zero or a value near zero at the time phase of the maximum inspiration at which the volume of the lung field is the maximum. The inventors have also found that the average of the pixel values of the difference image data increases to zero or a value near zero at the time phase of the maximum expiration at which the volume of the lung field is the minimum.

Thus, a time phase at which the average of the pixel values of the difference image data generated by the difference processing on the two-dimensional image data of the earlier one of two time phases adjacent to each other and the two-dimensional image data of the later one decreases to zero or a value near zero may be selected as the time phase of the maximum inspiration, and a time phase at which the average increases to zero or a value near zero may be selected as the time phase of the maximum expiration.

As described above, it is possible to easily determine the time phases of the maximum inspiration and the maximum expiration without extracting the lung field region from three-dimensional image data, thereby achieving a shortened time for processing image data and achieving an improved throughput.

According to the embodiment described above, it is possible to generate the two-dimensional image data of the first time phase Ph1 to the M-th time phase PhM from the three-dimensional image data of the first time phase Ph1 to the M-th time phase PhM in the breathing cycle of the subject obtained from the medical image diagnostic apparatus 110, and generate the difference image data of the first time phase Ph1 to the M-th time phase PhM by the difference processing on the pieces of two-dimensional image data of the first time phase Ph1 to the M-th time phase PhM and the two-dimensional image data of a reference time phase set from among the pieces of two-dimensional image data of the first time phase Ph1 to the M-th time phase PhM. Then, it is possible to calculate the average of the pixel values of the difference image data of the first time phase Ph1 to the M-th time phase PhM, so that the time phase of difference image data having the maximum average of the pixel values is selected as the time phase of the maximum inspiration of the subject, and the time phase of difference image data having the maximum average of the pixel values is selected as the time phase of the maximum expiration of the subject.

Accordingly, it is possible to easily determine predetermined time phases of inspiration and expiration without extracting the lung field region from three-dimensional image data, thereby achieving a shortened time for processing image data and achieving an improved throughput.

Second Embodiment

The first embodiment and the modification of the first embodiment describe that an image processing method is achieved by a medical image processing apparatus, but embodiments are not limited thereto. For example, the image processing method described in the first embodiment and the modification of the first embodiment may be achieved by the medical image diagnostic apparatus 110.

Figure 7:
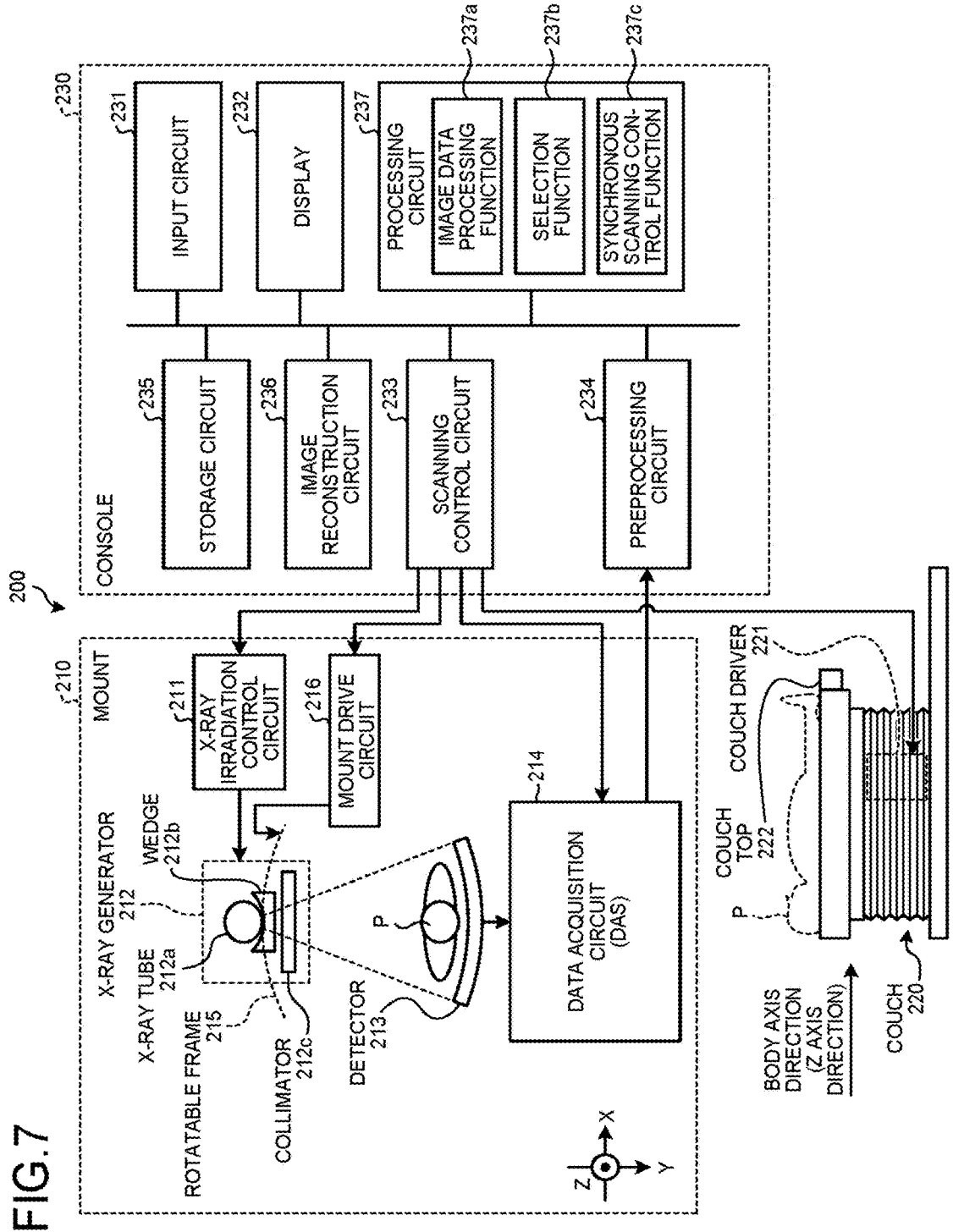
FIG. 7 is a block diagram of the configuration of an X-ray CT apparatus according to a second embodiment.

A second embodiment describes a case in which the image processing method is achieved by the medical image diagnostic apparatus 110. In the second embodiment, the medical image diagnostic apparatus 110 is an X-ray CT apparatus. FIG. 7 is a block diagram of an exemplary configuration of the X-ray CT apparatus according to the second embodiment.

FIG. 7 illustrates an exemplary configuration of an X-ray CT apparatus 200 according to the second embodiment. As illustrated in FIG. 7, the X-ray CT apparatus 200 according to the second embodiment includes a mount 210, a couch 220, and a console 230.

The mount 210 irradiates the subject P (patient) with X-ray, detects X-ray transmitted through the subject P, and outputs the detection result to the console 230. The mount 210 includes an X-ray irradiation control circuit 211, an X-ray generator 212, a detector 213, a data acquisition circuit (data acquisition system: DAS) 214, a rotatable frame 215, and a mount drive circuit 216. In the mount 210, a Cartesian coordinate system of an X axis, a Y axis, and a Z axis is defined as illustrated in FIG. 7. The X axis indicates the horizontal direction, the Y axis indicates the vertical direction, and the Z axis indicates the body axis direction of the subject P.

The rotatable frame 215 supports the X-ray generator 212 and the detector 213 opposite to each other across the subject P, and is a ring frame rotated fast in a circular orbit around the subject P by the mount drive circuit 216 to be described later.

The X-ray irradiation control circuit 211 is a device that serves as a high voltage generator and supplies an X-ray tube 212a with high voltage. The X-ray tube 212a generates X-ray using this high voltage supplied from the X-ray irradiation control circuit 211. The X-ray irradiation control circuit 211 adjusts the amount of X-ray emitted to the subject P by adjusting tube voltage and tube current supplied to the X-ray tube 212a under control of a scanning control circuit 233 to be described later.

The X-ray irradiation control circuit 211 performs switching of a wedge 212b. The X-ray irradiation control circuit 211 adjusts the emission range (fan angle and cone angle) of X-ray by adjusting the aperture of a collimator 212c. The present embodiment is applicable to a case in which an operator manually switches a plurality of kinds of wedges.

The X-ray generator 212 generates X-ray and irradiates the subject P with the generated X-ray. The X-ray generator 212 includes the X-ray tube 212a, the wedge 212b, and the collimator 212c.

The X-ray tube 212a is a vacuum tube that irradiates the subject P with an X-ray beam using high voltage supplied from the high voltage generator, as the rotatable frame 215 rotates. The X-ray tube 212a generates an X-ray beam spreading at a fan angle and a cone angle. For example, the X-ray tube 212a is capable of, under control of the X-ray irradiation control circuit 211, performing continuous irradiation of the entire circumference of the subject P with X-ray for a full reconstruction or with X-ray in a half-reconstructible irradiation range (180°+the fan angle) for a half reconstruction. The X-ray tube 212a is also capable of, under control of the X-ray irradiation control circuit 211, performing intermittent irradiation with X-ray (pulse X-ray) at a predetermined position (tube position). The X-ray irradiation control circuit 211 also capable of modulating the intensity of X-ray emitted from the X-ray tube 212a. For example, the X-ray irradiation control circuit 211 increases the intensity of X-ray emitted from the X-ray tube 212a at a particular tube position, and decreases the intensity of X-ray emitted from the X-ray tube 212a in a range except for this particular tube position.

The wedge 212b is an X-ray filter for adjusting the amount of X-ray emitted from the X-ray tube 212a. Specifically, the wedge 212b is a filter that transmits and attenuates the X-ray emitted from the X-ray tube 212a so that the X-ray emitted onto the subject P from the X-ray tube 212a has a predetermined distribution. The wedge 212b is, for example, an aluminum filter fabricated to have a predetermined target angle and a predetermined thickness. The wedge is also called a wedge filter or a bow-tie filter.

The collimator 212c is a slit for narrowing, under control of the X-ray irradiation control circuit 211, the emission range of X-ray having its amount adjusted by the wedge 212b.

The mount drive circuit 216 rotates the rotatable frame 215 to rotate the X-ray generator 212 and the detector 213 in a circular orbit around the subject P.

The detector 213 is a two-dimensional array detector (planar detector) that detects X-ray transmitted through the subject P, in which a plurality of detection element arrays each including X-ray detection elements corresponding to a plurality of channels are arranged along the body axis direction of the subject P (the Z axis direction illustrated in FIG. 7). Specifically, the detector 213 in the second embodiment includes a plurality of (320, for example) arrays of X-ray detection elements arranged along the body axis direction of the subject P, and is capable of detecting the X-ray transmitted through the subject P in a wide range including, for example, the lungs and heart of the subject P.

The data acquisition circuit 214 is a DAS and acquires projection data from detection data of X-ray detected by the detector 213. The data acquisition circuit 214 performs, for example, amplification, A/D conversion, and sensitivity correction between channels on X-ray intensity distribution data detected by the detector 213 so as to generate projection data. The data acquisition circuit 214 then transmits the generated projection data to the console 230 to be described later. For example, when X-ray is continuously emitted from the X-ray tube 212a while the rotatable frame 215 rotates, the data acquisition circuit 214 acquires projection data set for the entire circumference (360°). The data acquisition circuit 214 associates each piece of the acquired projection data with the tube position, and transmits the data to the console 230 to be described later. The tube position is information indicating a projection direction of the projection data. The sensitivity correction between channels may be performed by a preprocessing circuit 234 to be described later.

The couch 220 is a device on which the subject P is placed, and includes a couch driver 221 and a couchtop 222 as illustrated in FIG. 7. The couch driver 221 moves the couchtop 222 in the Z axis direction to move the subject P into the rotatable frame 215. The couchtop 222 is a board on which the subject P is placed.

The mount 210 performs, for example, helical scanning that helically scans the subject P by rotating the rotatable frame 215 while moving the couchtop 222. Alternatively, the mount 210 performs conventional scanning that scans the subject P in a circular orbit by rotating the rotatable frame 215 while fixing the position of the subject P after having moved the couchtop 222. Alternatively, the mount 210 performs a step and shoot technique that moves the position of the couchtop 222 at a constant interval to perform conventional scanning of a plurality of scanning areas.

The console 230 is a device that receives an operation of the X-ray CT apparatus 200 by the operator and reconstructs X-ray CT image data using the projection data acquired by the mount 210. The console 230 includes an input circuit 231, a display 232, the scanning control circuit 233, the preprocessing circuit 234, a storage circuit 235, an image reconstruction circuit 236, and a processing circuit 237 as illustrated in FIG. 7.

The input circuit 231 includes, for example, a mouse, a keyboard, a track ball, a switch, a button, and a joystick used by the operator of the X-ray CT apparatus 200 to input various instructions and various settings, and transfers information of instructions and settings received from the operator to the processing circuit 237. For example, the input circuit 231 receives, from the operator, an image capturing condition of X-ray CT image data, a reconstruction condition for reconstructing the X-ray CT image data, and a condition of image processing on the X-ray CT image data. The input circuit 231 also receives an operation of selecting an examination on the subject P. The input circuit 231 also receives a specifying operation of specifying a site on an image.

The display 232 is a monitor viewed by the operator and displays, under control of the processing circuit 237, image data generated from X-ray CT image data to the operator, and a graphical user interface (GUI) to receive, for example, various instructions and various settings from the operator through the input circuit 231. The display 232 also displays, for example, a plan screen of a scanning plan and a screen for a scan being performed.

The scanning control circuit 233 controls, under control of the processing circuit 237, operations of the X-ray irradiation control circuit 211, the mount drive circuit 216, the data acquisition circuit 214, and the couch driver 221 so as to control the acquisition of projection data in the mount 210. Specifically, the scanning control circuit 233 controls the acquisition of projection data at image capturing that acquires a positioning image (scanogram image) and at main image capturing (scanning) that acquires an image used in diagnosis. For example, the scanning control circuit 233 acquires three-dimensional image data of a plurality of time phases in at least one breathing cycle by imaging the chest including the lungs and bronchi of the subject P. In other words, the scanning control circuit 233 acquires image data of a plurality of time phases on the subject. The scanning control circuit 233 is also referred to as acquisition circuitry.

The preprocessing circuit 234 performs, on the projection data generated by the data acquisition circuit 214, a logarithmic conversion and corrections such as offset correction, sensitivity correction, and beam hardening correction so as to generate corrected projection data. Specifically, the preprocessing circuit 234 generates corrected projection data of the positioning image generated by the data acquisition circuit 214 and corrected projection data acquired by the main image capturing, and stores the corrected projection data in the storage circuit 235.

The storage circuit 235 stores therein the projection data generated by the preprocessing circuit 234. Specifically, the storage circuit 235 stores therein the projection data of the positioning image generated by the preprocessing circuit 234 and the projection data for diagnosis acquired by the main image capturing. The storage circuit 235 also stores therein image data generated by the image reconstruction circuit 236 to be described later. The storage circuit 235 also stores therein, as necessary, a result of processing by the processing circuit 237 to be described later.

The image reconstruction circuit 236 reconstructs X-ray CT image data using projection data stored in the storage circuit 235. Specifically, the image reconstruction circuit 236 reconstructs X-ray CT image data from the projection data of the positioning image and the projection data of the image used in diagnosis. Various kinds of methods are available for this reconstruction, including a back projection. The back projection is performed by, for example, a filtered back projection (FBP) method. Alternatively, the image reconstruction circuit 236 may apply a successive approximation to reconstruct X-ray CT image data.

The image reconstruction circuit 236 performs various kinds of image processing on X-ray CT image data to generate image data. Then, the image reconstruction circuit 236 stores reconstructed X-ray CT image data and image data generated by various kinds of image processing in the storage circuit 235. For example, the image reconstruction circuit 236 generates two-dimensional image data illustrating a cross-section at, for example, the central position corresponding to a specifying input in the body axis direction for the three-dimensional image data of the first time phase Ph1 to the M-th time phase PhM.

The processing circuit 237 performs an entire control of an X-ray CT apparatus 200 by controlling operations of the mount 210, the couch 220, and the console 230. Specifically, the processing circuit 237 controls the scanning control circuit 233 to control CT scanning performed in the mount 210. The processing circuit 237 also controls the image reconstruction circuit 236 to control an image reconstruction and an image generation in the console 230. The processing circuit 237 also performs a control to display various kinds of image data stored in the storage circuit 235 on the display 232.

The processing circuit 237 executes an image data processing function 237a, a selection function 237b, and a synchronous scanning control function 237c as illustrated in FIG. 7. For example, processing functions executed by the image data processing function 237a, the selection function 237b, and the synchronous scanning control function 237c as components of the processing circuit 237 illustrated in FIG. 7 are recorded in the storage circuit 235 in the form of a computer-executable program. The processing circuit 237 is a processor that reads out each computer program from the storage circuit 235 and executes the computer program to achieve the function corresponding to the computer program. In other words, having read out the computer programs, the processing circuit 237 has the functions in the processing circuit 237 in FIG. 7. The image data processing function 237a is also referred to as image data processing circuitry, the selection function 237b is also referred to as association circuitry, and the synchronous scanning control function 237c is also referred to as synchronous scanning control circuitry.

The image data processing function 237a executes the same functions as those of the image data processing circuit 40 and the measurement circuit 50 according to the first embodiment. In other words, the image data processing function 237a calculates an index value obtained by comparing the pixel value of image data of a reference time phase among pieces of image data of a plurality of time phases and the pixel value of each of the pieces of image data of the time phases.

The selection function 237b executes the same function as the selection circuit 60 according to the first embodiment. In other words, the selection function 237b selects at least one of the pieces of image data of the time phases based on the index value obtained at each time phase, and associates the one piece of image data with a breathing time phase in at least one of inspiration and expiration of the subject P.

For example, the image data processing function 237a performs difference processing on image data of each time phase and image data of a reference time phase to calculate an index value. Then, the selection function 237b selects a time phase at which the index value calculated by the image data processing function 237a is the maximum as the time phase of the maximum inspiration of the subject. The selection function 237b also selects a time phase at which the index value calculated by the image data processing function 237a is the minimum as the time phase of the maximum expiration of the subject.

The reference time phase may be one of two time phases adjacent to each other among a plurality of time phases. In this case, for example, the image data processing function 237a performs difference processing on image data of the reference time phase and image data of the other time phase to calculate an index value. Then, the selection function 237b selects a time phase at which the index value calculated by the image data processing function 237a decreases to zero or a value near zero as the time phase of the maximum inspiration of the subject. The selection function 237b also selects a time phase at which the index value calculated by the image data processing function 237a increases to zero or a value near zero as the time phase of the maximum expiration of the subject.

Then, the image data processing function 237a extracts any pixel in the bronchi region included in two-dimensional image data of the time phases of the maximum inspiration and the maximum expiration selected by the selection function 237b. Then, the image data processing function 237a calculates, for example, the cross-sectional area of the extracted bronchial region and displays the calculation result on the display 232. In this case, the display 232 displays, for example, three-dimensional image data illustrating the bronchi of the subject, a marker indicating a specified position in the bronchial pathway direction, the pieces of two-dimensional image data of the first time phase Ph1 to the M-th time phase PhM, identification information for identifying the time phases of the maximum inspiration and the maximum expiration among the first time phase Ph1 to the M-th time phase PhM, and the cross-sectional areas of the bronchi in the maximum inspiration and the maximum expiration.

The configuration of the X-ray CT apparatus 200 according to the second embodiment is described above. With this configuration, the X-ray CT apparatus 200 according to the second embodiment acquires three-dimensional image data of a plurality of time phases in at least one breathing cycle by imaging the chest including the lungs and bronchi of the subject. The X-ray CT apparatus 200 may be used for the breathing synchronous scanning to image the chest including the lungs and bronchi of the subject.

The breathing synchronous scanning typically scans in durations of the maximum inspiration and the maximum expiration. For example, in the breathing synchronous scanning, the X-ray CT apparatus 200 acquires the breathing waveform of the subject P from a breathing detection apparatus, and scans at the time phases of the maximum inspiration and the maximum expiration. However, the breathing waveform acquired from the breathing detection apparatus may not be accurate in some cases. In such a case, the X-ray CT apparatus 200 may not be able to scan at the time phases of the maximum inspiration and the maximum expiration of the subject when the scan is based on the breathing waveform acquired from the breathing detection apparatus. Thus, in the second embodiment, the X-ray CT apparatus 200 uses the image data processing function 237a, the selection function 237b, and the synchronous scanning control function 237c to perform a control to scan at the time phases of the maximum inspiration and the maximum expiration of the subject. FIG. 8 illustrates the second embodiment.

In the X-ray CT apparatus 200 according to the second embodiment, the scanning control circuit 233 sequentially acquires image data of a plurality of time phases on the subject under an X-ray irradiation condition of preliminary image capturing to perform the breathing synchronous scanning. For example, the scanning control circuit 233 sequentially acquires three-dimensional image data of the first time phase Ph1 to the M-th time phase PhM under a low-dose X-ray irradiation condition. Then, the image reconstruction circuit 236 generates two-dimensional image data using the three-dimensional image data acquired by the scanning control circuit 233. For example, as illustrated in the diagrams on the top row of FIG. 8, the image reconstruction circuit 236 generates the two-dimensional image data of the time phase Ph1 from the three-dimensional image data of the time phase Ph1, generates the two-dimensional image data of the time phase Ph2 from the three-dimensional image data of the time phase Ph2, and generates the two-dimensional image data of the time phase PhM from the three-dimensional image data of the time phase PhM.

Subsequently, the image data processing function 237a calculates an index value each time image data of a new time phase is acquired. For example, the image data processing function 237a generates difference image data by difference processing on two-dimensional image data of two time phases adjacent to each other as illustrated in the diagrams on the middle row of FIG. 8, and calculates an average CT value of the generated difference image data as described in the lower part of FIG. 8. For example, when the two-dimensional image data of the time phase Ph2 is generated, the image data processing function 237a generates difference image data of the two-dimensional image data of the time phase Ph1 and the two-dimensional image data of the time phase Ph2, and calculates the average of the pixel values of the generated difference image data. Similarly, when the two-dimensional image data of the time phase PhM is generated, the image data processing function 237a generates difference image data of the two-dimensional image data of the time phase PhM−1 and the two-dimensional image data of the time phase PhM, and calculates the average of the pixel values of the generated difference image data.

Then, each time an index value is calculated, the selection function 237b determines whether image data of a new time phase is the image data corresponding to a breathing time phase of at least one of the maximum inspiration and the maximum expiration of the subject. For example, the selection function 237b determines a time phase at which the average CT value changes from positive to negative as the breathing time phase of the maximum inspiration, and determines a time phase at which the average CT value changes from negative to positive as the breathing time phase of the maximum expiration.

Then, if the image data of the new time phase is the breathing time phase of at least one of the maximum inspiration and the maximum expiration, the synchronous scanning control function 237c acquires, through the scanning control circuit 233, image data on the subject under an X-ray irradiation condition of the main image capturing. FIGS. 9A and 9B illustrate timing of the breathing synchronous scanning according to the second embodiment.

FIGS. 9A and 9B are graphs illustrating the average of the pixel values of the difference image data of each time phase generated by difference processing on two-dimensional image data of two time phases adjacent to each other. In FIGS. 9A and 9B, a horizontal axis represents the time phase, and a vertical axis represents the CT value in the "HU". In an example illustrated in FIG. 9A, the selection function 237b determines the fourth time phase as the maximum inspiration and determines the eighth time phase as the maximum expiration. In this case, the synchronous scanning control function 237c acquires, through the scanning control circuit 233, the image data on the subject under the X-ray irradiation condition of the main image capturing at the fourth time phase at which the maximum inspiration occurs. The synchronous scanning control function 237c also acquires, through the scanning control circuit 233, the image data on the subject under the X-ray irradiation condition of the main image capturing at the eighth time phase at which the maximum expiration occurs.

Similarly to the example illustrated in FIG. 9A, in an example illustrated in FIG. 9B, the selection function 237b determines the first time phase as the maximum inspiration and determines the seventh time phase as the maximum expiration. In this case, the synchronous scanning control function 237c acquires, through the scanning control circuit 233, the image data on the subject under the X-ray irradiation condition of the main image capturing at the first time phase at which the maximum inspiration occurs. The synchronous scanning control function 237c also acquires, through the scanning control circuit 233, the image data on the subject under the X-ray irradiation condition of the main image capturing at the seventh time phase at which the maximum expiration occurs.

With this configuration, the X-ray CT apparatus 200 is capable of scanning under the X-ray irradiation condition of the main image capturing at the time phases of the maximum inspiration and the maximum expiration of the subject. Although the second embodiment described above describes the case of performing the difference processing on the two-dimensional image data of two time phases adjacent to each other, embodiments are not limited thereto. For example, the pieces of two-dimensional image data of the first time phase Ph1 to the M-th time phase PhM may be processed based on, for example, the two-dimensional image data of the first time phase Ph1 as a predetermined reference time phase from among the pieces of two-dimensional image data of the first time phase Ph1 to the M-th time phase PhM. In this case, the synchronous scanning control function 237c acquires, through the scanning control circuit 233, the image data on the subject under the X-ray irradiation condition of the main image capturing at the time phase of the maximum inspiration in which the index value is the maximum. The synchronous scanning control function 237c also acquires, through the scanning control circuit 233, the image data on the subject under the X-ray irradiation condition of the main image capturing at the time phase of the maximum expiration in which the index value is the minimum.

In the X-ray CT apparatus 200 according to the second embodiment, the processing circuit 237 may be configured not to execute the synchronous scanning control function 237c. In other words, in the X-ray CT apparatus 200 according to the second embodiment, the processing circuit 237 may be configured to perform the image data processing function 237a and the selection function 237b.

Third Embodiment

The embodiments described above describe the case of selecting at least one of pieces of image data of a plurality of time phases and associating the one piece of image data with the breathing time phase of at least one of inspiration and expiration of the subject. When three-dimensional image data of a plurality of time phases in at least one breathing cycle by imaging the chest including the lungs and bronchi of the subject P are acquired, the total amount of the acquired three-dimensional image data is large.

However, in diagnosis, images at the time phases of the maximum expiration and the maximum inspiration are typically used. Thus, it is sufficient if the three-dimensional image of the time phase of the maximum inspiration and the three-dimensional image of the time phase of the maximum expiration are stored. For this reason, in a third embodiment, the medical image processing apparatus 100 stores the three-dimensional image data corresponding to the breathing time phase of at least one of the maximum inspiration and the maximum expiration of the subject in predetermined storage circuitry.

The medical image processing apparatus 100 according to the third embodiment has the same configuration as that of the medical image processing apparatus 100 according to the first embodiment illustrated in FIG. 1 except that the selection circuit 60 is provided with some additional functions.

The following describes the additional functions provided to the selection circuit 60. FIG. 10 illustrates the third embodiment.

As illustrated in the diagrams in the top row of FIG. 10, the image data acquiring circuit 20 acquires three-dimensional image data of a plurality of time phases in at least one breathing cycle transmitted from the medical image diagnostic apparatus 110 such as an X-ray CT apparatus. Then, as illustrated in the diagrams in the middle row of FIG. 10, similarly to the first embodiment, the image data generating circuit 30 generates, for example, two-dimensional image data illustrating a cross-section at a specified position in the body axis direction of the subject from the three-dimensional image data of each time phase acquired by the image data acquiring circuit 20. Then, as illustrated in the diagrams in the bottom row of FIG. 10, the image data processing circuit 40 performs difference processing on the two-dimensional image data of the time phases generated by the image data generating circuit 30. FIG. 10 illustrates a case of performing difference processing on the pieces of two-dimensional image data of the first time phase Ph1 to the M-th time phase PhM when the time phase Ph1 is set as a reference time phase. The measurement circuit 50 calculates the average of the pixel values of the entire difference image data of the first time phase Ph1 to the M-th time phase PhM generated by the processing in the image data processing circuit 40.

Then, the selection circuit 60 according to the third embodiment selects the image data corresponding to the breathing time phase of at least one of the maximum inspiration and the maximum expiration of the subject from among the image data of the time phases based on an index value calculated for each time phase. In an example illustrated in FIG. 10, the selection circuit 60 according to the third embodiment selects a time phase at which the average CT value is the maximum as the maximum inspiration time phase, and selects a time phase at which the average CT value is the minimum as the maximum expiration time phase. Then, the selection circuit 60 according to the third embodiment stores the three-dimensional image data corresponding to the selected time phases of image data in the predetermined storage circuitry.

As described above, the medical image processing apparatus 100 according to the third embodiment reconstructs, for example, only a central slice of the three-dimensional image data, and selects the image data corresponding to the breathing time phase of at least one of the maximum inspiration and the maximum expiration of the subject from among the image data of the time phases based on the index value. Then, the medical image processing apparatus 100 according to the third embodiment stores the three-dimensional image data corresponding to the time phase of the selected image data in the predetermined storage circuitry. As a result, the medical image processing apparatus 100 according to the third embodiment can reduce the total amount of stored three-dimensional image data.

In the third embodiment described above, in the medical image processing apparatus 100, the selection circuit 60 stores the three-dimensional image data corresponding to the breathing time phase of at least one of the maximum inspiration and the maximum expiration of the subject in the predetermined storage circuitry, but embodiments are not limited thereto. For example, the selection function 237*b* of the X-ray CT apparatus 200 may execute the same function as that of the selection circuit 60 according to the third embodiment.

Other Embodiments

Embodiments are not limited to the embodiments described above. The following description is made on the medical image processing apparatus 100 as an example, but other embodiments described below are similarly applicable to the X-ray CT apparatus 200.

Figure 11:
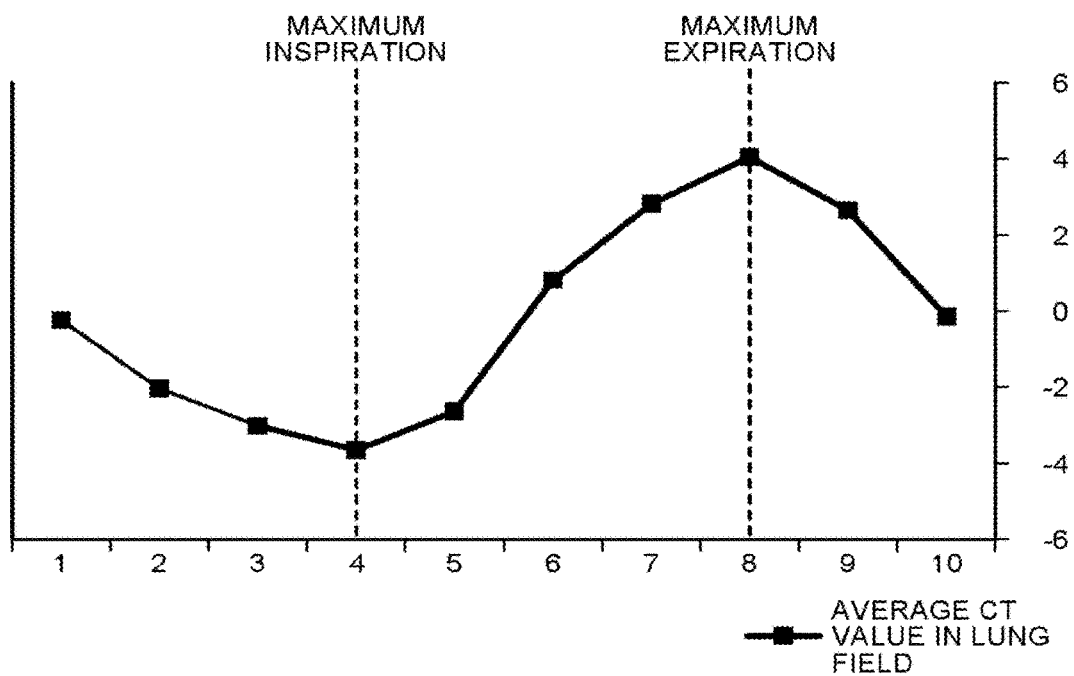
FIG. 11 is a diagram illustrating another embodiment.
Figure 12:
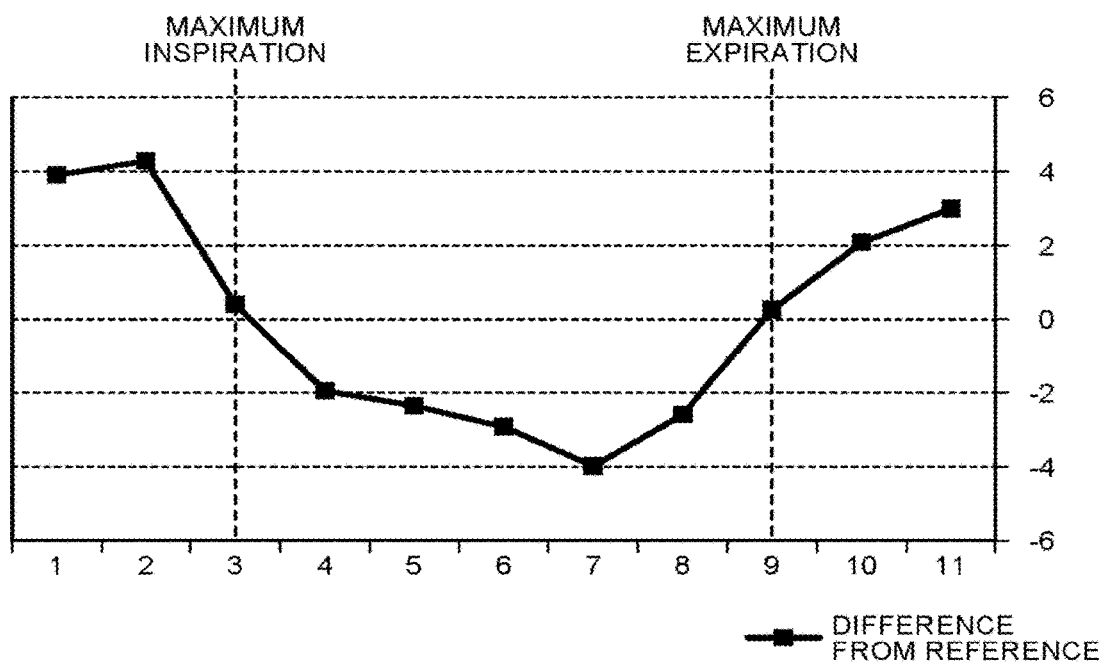
FIG. 12 is a diagram illustrating another embodiment.

The embodiments described above describe the example in which the time phases of the maximum inspiration and the maximum expiration are determined, but embodiments are not limited thereto. For example, when an image of the time phase of the maximum inspiration and an image of the time phase of the maximum expiration are to be displayed, the selection circuit 60 of the medical image processing apparatus 100 may further generate information including each time phase and the index value at the time phase in association with each other, and output the information through a predetermined display. FIGS. 11 and 12 illustrate other embodiments.

FIG. 11 illustrates a case of performing difference processing on pieces of two-dimensional image data of the first time phase Ph1 to the M-th time phase PhM with the time phase Ph1 being set as a reference time phase. In FIG. 11, the horizontal axis represents the time phase, and the vertical axis represents the CT value in the "HU". As illustrated in FIG. 11, the selection circuit 60 further displays a graph of the average of the pixel values of the difference image data of the time phases. In an example illustrated in FIG. 11, the eighth time phase at which the CT value is the maximum corresponds to the maximum inspiration, and the fourth time phase at which the CT value is the minimum corresponds to the maximum expiration. In this case, the selection circuit 60 may display information indicating the maximum inspiration and information indicating the maximum expiration. More specifically, the selection circuit 60 displays a dashed line and text information indicating that the eighth time phase corresponds to the maximum inspiration, and displays a dashed line and text information indicating that the fourth time phase corresponds to the maximum expiration.

FIG. 12 illustrates a case of performing difference processing on two-dimensional image data of time phases adjacent to each other. In FIG. 12, the horizontal axis represents the time phase, and the vertical axis represents the CT value in the "HU". As illustrated in FIG. 12, the selection circuit 60 further displays a graph of the average of the pixel values of the difference image data of the time phases. In an example illustrated in FIG. 12, the third time phase at which the average CT value changes from positive to negative corresponds to the maximum inspiration, and the ninth time phase at which the average CT value changes from negative to positive corresponds to the maximum expiration. In this case, similarly, the selection circuit 60 may display information indicating the maximum inspiration and information indicating the maximum expiration. More specifically, the selection circuit 60 displays a dashed line and text information indicating that the third time phase corresponds to the maximum inspiration, and displays a dashed line and text information indicating the ninth time phase corresponds to the maximum expiration. The selection circuit 60 may display only one of the dashed line and the text information indicating the maximum inspiration, and may display only one of the dashed line and the text information indicating the maximum expiration. Alternatively, the selection circuit 60 may display only one of the information indicating the maximum inspiration and the information indicating the maximum expiration.

Figure 13:
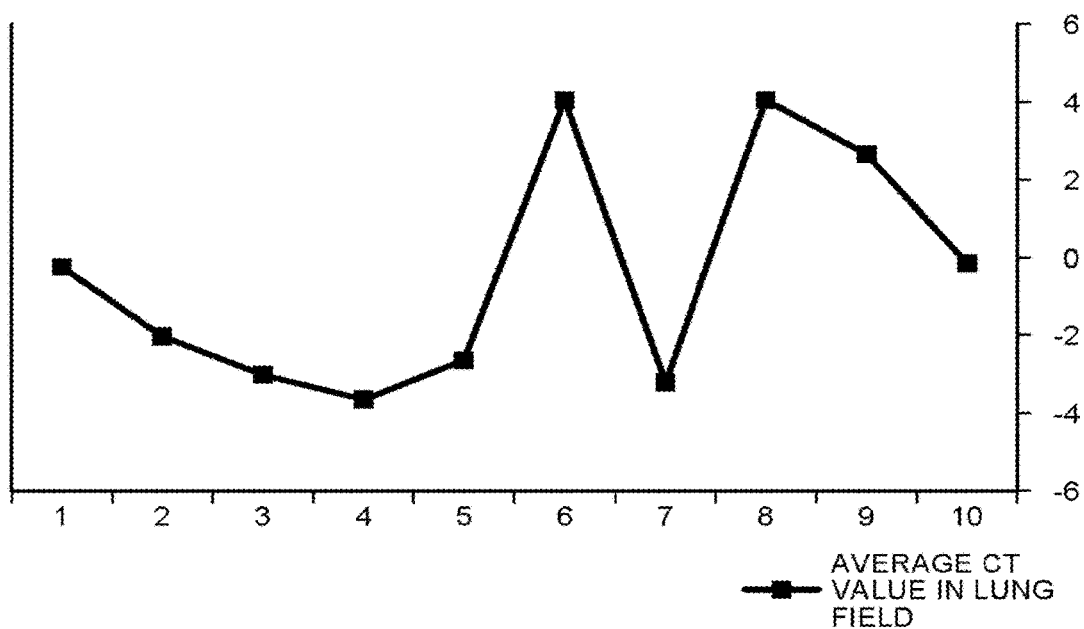
FIG. 13 is a diagram illustrating another embodiment.
Figure 14:
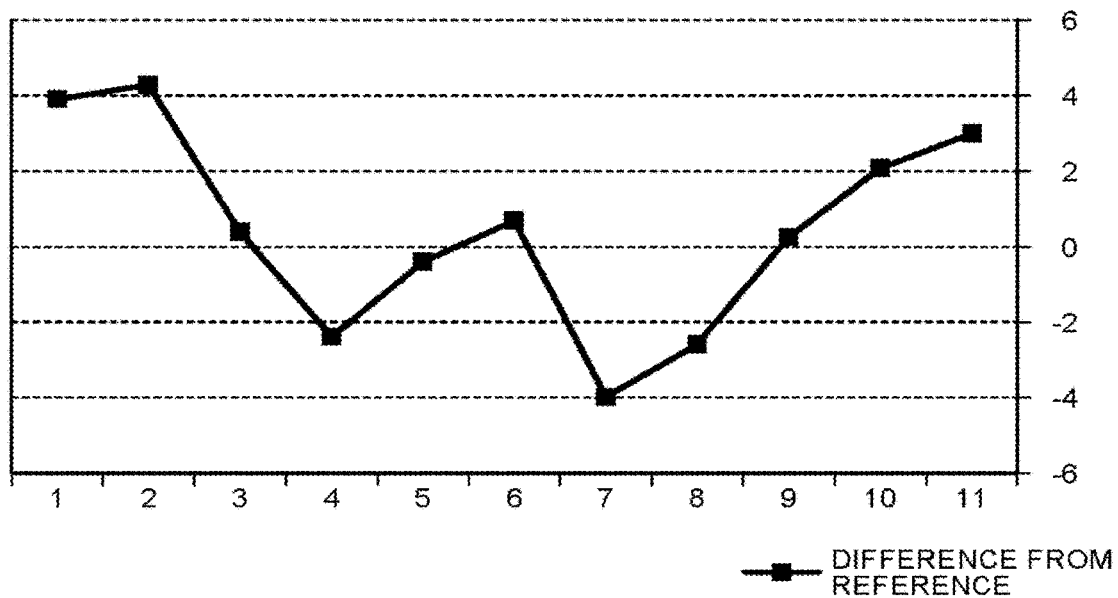
FIG. 14 is a diagram illustrating another embodiment.

The embodiments described above describe the cases in which the time phases of the maximum inspiration and the maximum expiration can be specified, but embodiments are not limited thereto. For example, for a subject having illness in the lungs, the time phases of the maximum inspiration and the maximum expiration may be shifted as compared to a normal subject in some cases. FIGS. 13 and 14 illustrate other embodiments.

FIG. 13 illustrates a case of performing difference processing on pieces of two-dimensional image data of the first time phase Ph1 to the M-th time phase PhM with the time phase Ph1 being set as a reference time phase. In FIG. 13, the horizontal axis represents the time phase, and the vertical axis represents the CT value in the "HU". As illustrated in FIG. 13, the selection circuit 60 further displays a graph of the average of the pixel values of the difference image data of the time phases. In an example illustrated in FIG. 13, the CT value is the maximum at the sixth time phase and the eighth time phase and the minimum at the fourth time phase and the seventh time phase. When a plurality of candidates are detected for at least one of the time phases of the maximum inspiration and the maximum expiration as described above, the selection circuit 60 outputs, through predetermined output circuitry, information indicating that the time phases of the maximum inspiration and the maximum expiration cannot be selected.

FIG. 14 illustrates a case of performing difference processing on two-dimensional image data of two time phases adjacent to each other. In FIG. 14, the horizontal axis represents the time phase, and the vertical axis represents the CT value in the "HU". As illustrated in FIG. 14, the selection circuit 60 further displays a graph of the average of the pixel values of the difference image data of the time phases. In an example illustrated in FIG. 14, the average CT value changes from positive to negative at the third time phase and the sixth time phase, and changes from negative to positive at the fifth time phase and the ninth time phase. When a plurality of candidates are detected for at least one of the time phases of the maximum inspiration and the maximum expiration as described above, the selection circuit 60 outputs, through the predetermined output circuitry, information indicating that the time phases of the maximum inspiration and the maximum expiration cannot be selected.

In the above description, the image data generating circuit 30 generates two-dimensional image data illustrating a cross-section (axial section) of three-dimensional image data in the body axis direction, but embodiments are not limited thereto. For example, the image data generating circuit 30 may generate, in place of two-dimensional image data illustrating an axial section, two-dimensional image data illustrating a cross-section (sagittal section) of three-dimensional image data in a sagittal direction or two-dimensional image data illustrating a cross-section (coronal section) of three-dimensional image data in a coronal direction. In this case, similarly to the processing of generating difference image data from two-dimensional image data illustrating the axial section, the image data processing circuit 40 generates difference image data from two-dimensional image data illustrating the sagittal section or two-dimensional image data illustrating the coronal section. Then, similarly to the processing of calculating an index value using the difference image data generated from the axial section, the measurement circuit 50 calculates, for each time phase, an index value using difference image data generated from the sagittal section or the coronal section. When generating two-dimensional image data illustrating the sagittal section or two-dimensional image data illustrating the coronal section, the image data generating circuit 30 desirably generates the sagittal section or the coronal section at a position at which the lung field will be imaged, similarly to generation of two-dimensional image data illustrating the axial section. For example, the image data generating circuit 30 generates the sagittal section or the coronal section of three-dimensional image data at the central position.

The embodiments described above describe the cases in which the image data generating circuit 30 generates a single two-dimensional image for each time phase, but embodiments are not limited thereto. In other words, the image data generating circuit 30 may generate two-dimensional image data illustrating a plurality of cross-sections at each time phase.

For example, the image data generating circuit 30 may generate two-dimensional image data illustrating a plurality of cross-sections in the body axis direction. More specifically, the image data generating circuit 30 generates, in addition to a two-dimensional image illustrating a cross-section at the central position in the body axis direction, two two-dimensional image data illustrating cross-sections at positions in front of and behind this central position in the body axis direction. In this case, the image data processing circuit 40 generates difference image data for each of a plurality of cross-sections at each time phase. In other words, the image data processing circuit 40 uses the three two-dimensional image data generated by the image data generating circuit 30 for each of the first time phase Ph1 to the M-th time phase PhM to generate three pieces of difference image data of the time phase. More specifically, the image data processing circuit 40 generates difference image data at the central position in the body axis direction, difference image data at a position in front of this central position, and difference image data at a position behind this central position for each time phase. Then, the measurement circuit 50 calculates an index value using difference image data generated for each cross-section at each time phase, and calculates the average of the index values calculated for the cross-sections, thereby determining the calculation result as the index value for the time phase. More specifically, the measurement circuit 50 calculates an index value that is the average of the pixel values of the entire difference image data of each time phase generated by the processing in the image data processing circuit 40, and calculates the average of the calculated index values, thereby determining the calculation result as the index value for the time phase. The number of two-dimensional image data generated for each time phase by the image data generating circuit 30 can be optionally changed.

The image data generating circuit 30 may generate two-dimensional image data illustrating the sagittal section and two-dimensional image data illustrating the coronal section in addition to two-dimensional image data illustrating the axial section. In this case, the image data processing circuit 40 generates difference image data from two-dimensional image data illustrating the axial section, generates difference image data from two-dimensional image data illustrating the sagittal section, and generates difference image data from two-dimensional image data illustrating the coronal section. Then, the measurement circuit 50 calculates an index value of the difference image data of the section in each direction for each time phase, and calculates the average of the calculated index values, thereby determining the calculation result as the index value for the time phase. Although the above description is made on the example in which the image data processing circuit 40 generates difference image data using the axial section, the sagittal section, and the coronal section, a combination of the directions of the sections used to generate difference image data can be optionally changed. In addition, the image data processing circuit 40 may use optionally different numbers of two-dimensional image data to generate difference image data between the axial section, the sagittal section, and the coronal section.

The embodiments described above describe the cases of using pixels of the entire two-dimensional image data, but embodiments are not limited thereto. For example, the measurement circuit 50 may use only any pixel existing in a region of interest set by the operator. In other words, the measurement circuit 50 performs difference processing on any pixel in a region defined in image data of each time phase.

The pieces of two-dimensional image data of the first time phase Ph1 to the M-th time phase PhM and the two-dimensional image data of the first time phase Ph1 may be subjected to addition, multiplication, or division.

The embodiments described above describe the case in which generating a difference image data to calculate an index value, but embodiments are not limited thereto. For example, the measurement circuit 50 may perform difference processing of calculating a difference between the sum of the pixel values of the image data of the reference time phase and the sum of the pixel values of image data of each of a plurality of time phases, and set the calculated difference as an index value. In other words, the measurement circuit 50 calculates the sum of the pixel values of the entire difference image data of each of the first time phase Ph1 to the M-th time phase PhM. Then, the selection circuit 60 may select the time phase of difference image data at which the sum of the pixel values is the maximum as the time phase of the maximum inspiration of the subject, and select the time phase of difference image data at which the sum of the pixel values is the minimum as the time phase of the maximum expiration of the subject.

In this case, the measurement circuit 50 may perform difference processing on any pixel having a CT value equal to or smaller than a predetermined threshold in image data of each of a plurality of time phases. More specifically, the measurement circuit 50 calculates the sum of the pixel values of any pixels each having a CT value equal to or smaller than −100, and then performs difference processing.

Difference image data of the first time phase Ph1 to the M-th time phase PhM is generated by difference processing on the three-dimensional image data of each of the first time phase Ph1 to the M-th time phase PhM and, for example, the three-dimensional image data of the first time phase Ph1 as a reference time phase, and then the average of the pixel values of the generated difference image data of each of the first time phase Ph1 to the M-th time phase PhM is calculated. Then, the time phase of difference image data at which the average of the pixel values is the maximum may be selected as the time phase of the maximum inspiration of the subject, and the time phase of difference image data at which the average of the pixel values is the minimum may be selected as the time phase of the maximum expiration of the subject.

In the above descriptions of the embodiments, each component of each apparatus illustrated in the figures is a functional concept and does not necessarily require a physical configuration as illustrated. In other words, specific modes of separation and integration of each apparatus are not limited to those illustrated, and the entire or part of the apparatus may be functionally or physically separated or integrated in optional units depending on various kinds of loads and use conditions. In addition, the entire or optional part of processing functionality provided in each apparatus may be achieved by a CPU and a computer program analyzed and executed by this CPU, or achieved as wired logic hardware.

The image processing method in the above descriptions of the embodiments may be achieved by executing a prepared image processing program on a computer such as a personal computer or a work station. This image processing program may be distributed over a network such as the Internet. This image processing program may also be recorded in a computer-readable recording medium such as a hard disk, a flexible disk (FD), a CD-ROM, a MO, or a DVD, and executed through reading out from the recording medium by a computer.

According to at least one of the embodiments described above, it is possible to achieve a shortened time for processing image data.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus, comprising:
storage circuitry configured to store therein pieces of X-ray image data on a subject obtained at a plurality of time phases from a medical image diagnostic apparatus; and
processing circuitry configured to
calculate an index value obtained by comparing a pixel value of X-ray image data of a reference time phase among the pieces of X-ray image data of the time phases and a pixel value of each of the pieces of X-ray image data of the time phases without extracting a lung field region of the subject from the nieces of X-ray image data, and
select at least one of the pieces of X-ray image data of the time phases based on the index value calculated for each of the time phases and associate the one piece of X-ray image data with a breathing time phase in at least one of inspiration and expiration of the subject, wherein
the reference time phase is any one of the time phases, and
the processing circuitry
performs difference processing on each of the pieces of X-ray image data of the time phases and the X-ray image data of the reference time phase to calculate the index value,
selects a time phase at which the index value calculated reaches the maximum value as a time phase of maximum inspiration of the subject, and
selects a time phase at which the index value calculated reaches the minimum value as a time phase of maximum expiration of the subject.

2. The medical image processing apparatus according to claim 1, wherein the processing circuitry
selects X-ray image data corresponding to a breathing time phase in at least one of the maximum inspiration and the maximum expiration of the subject from among the pieces of X-ray image data of the time phases based on the index value calculated for each of the time phases.

3. The medical image processing apparatus according to claim 1, wherein
the reference time phase is one of two time phases adjacent to each other among the time phases, and
the processing circuitry
performs difference processing on X-ray image data of the other time phase and X-ray image data of the reference time phase to calculate the index value,
selects a time phase at which the index value calculated decreases to zero or a value near zero as the time phase of maximum inspiration of the subject, and
selects a time phase at which the index value calculated increases to zero or a value near zero as the time phase of maximum expiration of the subject.

4. The medical image processing apparatus according to claim 2, wherein the processing circuitry performs the difference processing that includes generating a difference X-ray image data obtained by calculating a difference between pixel values of pixels at corresponding positions of the X-ray image data of the reference time phase and each of the pieces of X-ray image data of the time phases, and determining an average of pixel values of the generated difference X-ray image data as the index value.

5. The medical image processing apparatus according to claim 2, wherein the processing circuitry performs the difference processing that includes generating a difference X-ray image data obtained by calculating a difference between pixel values of pixels at corresponding positions of the X-ray image data of the reference time phase and each of the pieces of X-ray image data of the time phases, and determining a sum of pixel values of the generated difference X-ray image data as the index value.

6. The medical image processing apparatus according to claim 2, wherein the processing circuitry performs the difference processing that includes calculating a difference between a sum of pixel values of the X-ray image data of the reference time phase and a sum of pixel values of each of the pieces of X-ray image data of the time phases, and determining the calculated difference as the index value.

7. The medical image processing apparatus according to claim 6, wherein the processing circuitry performs the difference processing on any pixel having a computed tomography (CT) value not larger than a predetermined threshold in each of the pieces of X-ray image data of the time phases.

8. The medical image processing apparatus according to claim 2, wherein the processing circuitry performs the difference processing on any pixel in a region defined in each of the pieces of X-ray image data of the time phases.

9. The medical image processing apparatus according to claim 1, wherein the processing circuitry calculates the index value using, as the pieces of X-ray image data, two-dimensional X-ray image data obtained by imaging a chest of the subject, the two-dimensional X-ray image data including a lung field of the subject.

10. The medical image processing apparatus according to claim 9, wherein the processing circuitry calculates the index value using a plurality of pieces of two-dimensional X-ray image data as the pieces of X-ray image data.

11. The medical image processing apparatus according to claim 9, wherein the two-dimensional X-ray image data corresponds to at least one of an axial section, a sagittal section, and a coronal section of the subject.

12. The medical image processing apparatus according to claim 1, wherein the processing circuitry extracts a bronchial region in X-ray image data of a predetermined time phase associated by the processing circuitry.

13. The medical image processing apparatus according to claim 2, wherein the processing circuitry outputs, through predetermined output circuitry, information indicating that the time phases of the maximum inspiration and the maximum expiration are not selectable, when a plurality of candidates are detected for at least one of the time phases of the maximum inspiration and the maximum expiration.

14. The medical image processing apparatus according to claim 1, wherein the processing circuitry further generates information including each time phase and the index value at the time phase in association with each other and outputs the information through a predetermined display.

15. The medical image processing apparatus according to claim 1, wherein the processing circuitry selects X-ray image data corresponding to a breathing time phase in at least one of the maximum inspiration and the maximum expiration of the subject from among the pieces of X-ray image data of the time phases based on the index value calculated for each of the time phases and stores three-dimensional X-ray image data corresponding to a time phase of the selected X-ray image data in predetermined storage circuitry.

16. An X-ray computed tomography (CT) apparatus, comprising:
processing circuitry configured to
acquire pieces of X-ray image data on a subject at a plurality of time phases,
calculate an index value obtained by comparing a pixel value of X-ray image data of a reference time phase among the pieces of X-ray image data of the time phases and a pixel value of each of the pieces of X-ray image data of the time phases without extracting a lung field region of the subject from the pieces of X-ray image data, and
select at least one of the pieces of X-ray image data of the time phases based on the index value calculated for each of the time phases and associate the one piece of X-ray image data with a breathing time phase in at least one of inspiration and expiration of the subject, wherein
the reference time phase is any one of the time phases, and
the processing circuitry
performs difference processing on each of the pieces of X-ray image data of the time phases and the X-ray image data of the reference time phase to calculate the index value,
selects a time phase at which the index value calculated reaches the maximum value as a time phase of maximum inspiration of the subject, and
selects a time phase at which the index value calculated reaches the minimum value as a time phase of maximum expiration of the subject.

17. The X-ray CT apparatus according to claim 16, wherein
the processing circuitry
acquires pieces of X-ray image data on the subject at a plurality of time phases with an X-ray irradiation condition of preliminary image capturing,
calculates the index value each time X-ray image data of a new time phase is acquired,
determines, each time the index value is calculated, whether the X-ray image data of the new time phase corresponds to a breathing time phase in at least one of the maximum inspiration and the maximum expiration of the subject, and acquires X-ray image data on the subject with an X-ray irradiation condition of main image capturing when the X-ray image data of the new time phase corresponds to the breathing time phase in at least one of the maximum expiration and the maximum expiration.

18. The X-ray CT apparatus according to claim 16, wherein the processing circuitry selects X-ray image data corresponding to a breathing time phase in at least one of the maximum inspiration and the maximum expiration of the subject from among the pieces of X-ray image data of the time phases based on the index value calculated for each of the time phases and stores three-dimensional X-ray image data corresponding to a time phase of the selected X-ray image data in predetermined storage circuitry.

19. An image processing method, comprising:

storing, in storage circuitry, pieces of X-ray image data on a subject obtained at a plurality of time phases from a medical image diagnostic apparatus;

calculating an index value obtained by comparing a pixel value of X-ray image data of a reference time phase among the pieces of X-ray image data of the time phases and a pixel value of each of the pieces of X-ray image data of the time phases without extracting a lung field region of the subject from the pieces of X-ray image data;

selecting at least one of the pieces of X-ray image data of the time phases based on the index value calculated for each of the time phases and associating the one piece of X-ray image data with a breathing time phase in at least one of inspiration and expiration of the subject, the reference time phase being any one of the time phases;

performing difference processing on each of the pieces of X-ray image data of the time phases and the X-ray image data of the reference time phase to calculate the index value;

selecting a time phase at which the index value calculated reaches the maximum value as a time phase of maximum inspiration of the subject; and selecting a time phase at which the index value calculated reaches the minimum value as a time phase of maximum expiration of the subject.

* * * * *